United States Patent [19]
Grondin et al.

[11] Patent Number: 6,103,954
[45] Date of Patent: *Aug. 15, 2000

[54] LIQUID ACQUISITION LAYER FOR PERSONAL ABSORBENT ARTICLE

[75] Inventors: Pierre Grondin, Mooresville, N.C.; Samuel C. Baer, Germantown, Tenn.

[73] Assignee: FiberTechGroup, Inc., Landisville, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/933,234

[22] Filed: Sep. 18, 1997

[51] Int. Cl.[7] ........................................ A61F 13/15
[52] U.S. Cl. ........................... 604/370; 604/378; 604/365
[58] Field of Search ...................... 604/365, 372

[56] References Cited

U.S. PATENT DOCUMENTS

| | | | |
|---|---|---|---|
| 4,063,995 | 12/1977 | Grossman | 162/112 |
| 4,309,469 | 1/1982 | Varona | 428/74 |
| 4,362,781 | 12/1982 | Anderson | 428/291 |
| 4,447,570 | 5/1984 | Cook et al. | 524/127 |
| 4,886,579 | 12/1989 | Clark et al. | 162/111 |
| 4,925,722 | 5/1990 | Jeffers et al. | 428/131 |
| 4,959,894 | 10/1990 | Jeffers et al. | 28/104 |

*Primary Examiner*—John G. Weiss
*Assistant Examiner*—Dennis Ruhl
*Attorney, Agent, or Firm*—Pyle & Piontek

[57] ABSTRACT

A liquid acquisition layer is inserted between a porous cover sheet and an absorbent core of an absorbent article such as a disposable diaper. The liquid acquisition layer is made from polymer fibers bonded by an adhesive, with the adhesive rendered insoluble by curing. The cured adhesive has a glass transition temperature in excess of 30° C. and preferably above 37° C., which is normal body temperature. This allows the acquisition to remain resilient and retain void volume when heated by the body or body liquids.

5 Claims, 1 Drawing Sheet

LIQUID ACQUISITION LAYER FOR PERSONAL ABSORBENT ARTICLE

BACKGROUND OF THE INVENTION

This invention relates to fabric components used in personal absorbent articles such as diapers and feminine hygiene products, which are worn against the body of the user and are employed to absorb bodily liquids and exudates.

Disposable articles of this nature generally include an outer waterproof layer of film, an inner absorbent core, and a cover sheet made of nonwoven fabric. The absorbent core generally comprises cellulose pulp, and a variety of types of nonwovens have been used as the cover sheet, especially calendered or point bonded polyolefin webs of fibers. To provide requisite softness, the cover sheet typically comprises fibers in the range of 1.7 to 3.3 decitex. A smaller fiber would not provide adequate porosity in the fabric, and a fabric made up of a larger fiber would feel harsh against the skin.

Since the mid-1980's, superabsorbent polymers (SAP) have been incorporated into cellulose diaper cores. These polymers are capable of absorbing up to 40 times their weight in body liquids and are more cost effective than fluff pulp alone. The SAP particles are either mixed with the pulp or are incorporated by layering, and the structure is usually densified to reduce bulk.

With the advent of the use of SAP in absorbent cores, other problems have arisen. Dense core structures generally require a longer time to absorb liquids, and the SAP particles may swell and form gel blocks which impede the liquid acquisition rate of the core. A slow acquisition or absorption rate by the core may result in runoff and leakage of excess liquids.

In order to deal with the above problem, liquid acquisition layers have been employed, namely, a relatively porous and sometimes bulky layer of nonwoven fabric inserted between the cover sheet and the porous core. The pore size of the transfer layer is usually larger than the pore size of the cover sheet. The acquisition layer provides additional void volume for liquids at the interface into the core, and generally provides a more uniform distribution of liquids. This allows the cover sheet of the diaper to feel dry while the core is absorbing the liquid.

Nonwoven fabrics used in acquisition layers are made by a variety of methods, including thermal point bonding of polymer fibers, power bonding and through-air bonding. Adhesive bonding is also employed wherein a web of fibers is passed through or sprayed with an adhesive emulsion, and the emulsion is cured or set by heating. These cured adhesives are characterized by having a glass transition temperature, or Tg, at or above which the polymer chains are mobile or can freely rotate. Adhesives previously used in acquisition layers have had a Tg in the order of −5° C. to 20° C.

One important property of liquid acquisition layers is the ability to retain their compressive resiliency in both the dry and wet states. If the porous structure of the fabric collapses, the void volume is greatly reduced, and the fabric can no longer function as a transfer layer. For example, if the transfer layer suffers loss of resilience, void volume or porosity after an initial liquid insult, subsequent insults will not be accommodated, and the article will leak, even though there remains sufficient liquid capacity in the core to eventually absorb the excess liquid.

SUMMARY OF THE INVENTION

It has been found that the properties of adhesive bonded nonwoven fabrics used as liquid acquisition layers can be greatly improved by selection of an adhesive having a glass transition temperature in the cured state in excess of 30° C. and preferably near or above 37° C., which is normal body temperature. While these fabrics are somewhat stiff or harsh compared to fabrics bonded with softer adhesives, a problem does not arise, since the acquisition layer is covered by a relatively soft cover layer or fabric in contact with the body.

It is theorized that adhesively bonded acquisition fabrics having a relatively low Tg have adhesive bonds which are degraded by body heat or by the heat of body liquids, causing the fabric to lose its resilience and void volume. The fabrics of the present invention provide improved rewet characteristics at ambient and at body temperature and provide a distinct improvement over previous proposals.

In one preferred form of the present invention, an acquisition nonwoven fabric layer is disposed between an outer nonwoven cover layer and an absorbent core. The acquisition layer comprises polymer fibers having a denier of 3 to 15 bonded by a cured adhesive resin. The fibers, preferably polyester fibers, are first formed into a web by carding. The web is then treated with about 10 to about 40 percent of an aqueous emulsion of a adhesive binder having a Tg in excess of 30° C. The web is then dried by heating, such as by passing over steam cans, which renders the binder insoluble in water and bonds the fiber web together. The resulting fabric, having a preferred basis weight of from about 15 to about 60 grams per square meter (gsm) is incorporated into an absorbent product as aforesaid. The acquisition fabric layer is characterized by having the ability to retain structural integrity and compressive resilience at temperatures up to the temperature of the body and to temperatures of body liquids coming into contact with the acquisition layer.

In another aspect of the present invention, a liquid acquisition fabric is provided, said fabric preferably comprising polyester fibers having a denier in excess of 3, and a cured adhesive bonding said fibers together and having a Tg in excess of 30° C, and preferably in excess of 37° C. The preferred binder is styrene-butadiene copolymer having a styrene content in excess of 70%.

DETAILED DESCRIPTION OF THE INVENTION

Figure 1:
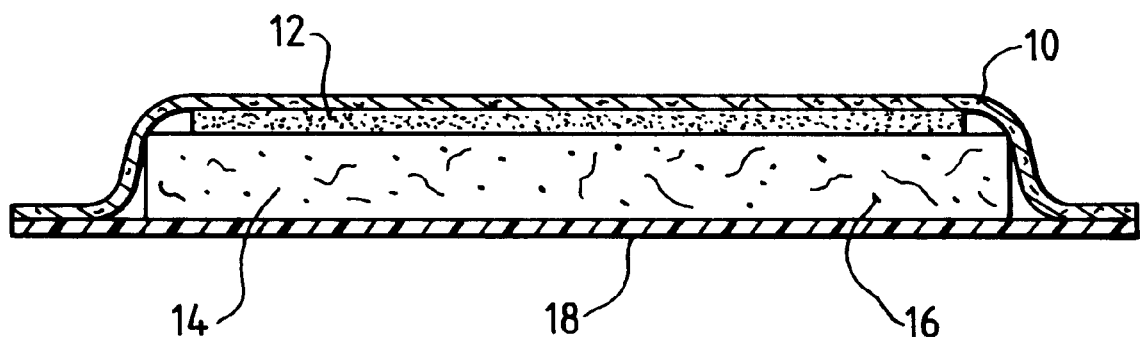
FIG. 1 is a cross sectional view of an absorbent article having the liquid acquisition layer of the present invention.

FIG. 1 illustrates the basic components of a disposable liquid absorbing article used for a variety of sanitary purposes, such as infant diapers, adult incontinence briefs and feminine sanitary protection pads. A porous top or cover sheet 10 is disposed over an absorbent core 14 containing fluff pulp and SAP particles 16. A liquid transfer layer 12 is disposed between the cover sheet 10 and the core 14. The outwardly facing surface of the core 14 may be covered by a layer of impermeable or microporous film 18 to prevent outward escape of liquids. The cover sheet 10 is preferably soft to the touch and may comprise a web of 1.7 to 3.3 denier polypropylene fibers or filaments bonded together by thermal embossing in which the web is passed through the nip of a pair of heated steel calender rolls, with one of the rolls being engraved.

In accordance with the present invention, the liquid transfer layer 12 is a nonwoven fabric of polymer fibers bonded together by a cured adhesive bonding agent, said bonding agent having a glass transition temperature or Tg in excess of about 30° C. and most preferably in excess of about 37° C., the normal temperature of the human body.

The liquid transfer layer 12 is preferably a nonwoven web of polyester fibers having a denier greater than 3 and preferably in the range of about 6 to about 15. The basis weight of the web is from about 15 to about 60 grams per square meter (gsm) and the weight percent of the binder resin is from about 10 to about 40 of the basis weight of the finished web. The binder resin is preferably furnished in the form of an aqueous emulsion, and the emulsion is uniformly coated or sprayed onto the web. The web is then dried by heating, such as by passing the web over steam cans, through a hot air oven, or under infrared heating lamps, whereupon the adhesive is cured and rendered insoluble to water.

The most preferred bonding resin is a styrene-butadiene copolymer having a Tg in excess of 30°C. and a styrene content in excess of 70%. Other binders are available and include vinyl chloride, vinyl copolymers, as well as acrylic polymers and copolymers.

The fibers are first formed into a continuous web by carding or air laying. The web may first be treated with a dilute solution of a surfactant by passing the web through a pair of coating rolls. The prewetted web is then coated or otherwise treated with the binder and dried.

In a most preferred embodiment, the web comprises 65–85% polyester fibers which are 6 denier or greater and 25–35% styrene-butadiene copolymer that has a Tg of 35° to 45° and a styrene content in excess of 70–75%

While the liquid acquisition fabric layer of the present invention is stiffer than fabrics generally used for the same purpose, advantage is taken of the fact that the acquisition layer is covered by the cover sheet 10, and the acquisition layer will have a pore size greater than the cover sheet.

In further illustration of the present invention, the following example is given.

EXAMPLE

A series of webs of polyester fibers having a denier of 6 were produced, and a target basis weight of 32 and 43 gsm. The finished webs were bonded with styrene-butadiene copolymer having a Tg of 20°, 30° and 40° C. as indicated in the following tables. The physical properties of the fabrics were set forth in the following table.

| Binder Tg (C) | Basis Weight gsm | Caliper mils | CD Tensile gr/in | CD Stretch % | MD Tensile gr/in | MD Stretch % | Styrene Content % |
|---|---|---|---|---|---|---|---|
| 20 | 38.85 | 25.95 | 206 | 113 | 1932 | 12.37 | 66 |
| 20 | 29.73 | 16.72 | 212 | 103 | 1907 | 13.36 | 66 |
| 30 | 29.46 | 15.51 | 187 | 106 | 1935 | 18.86 | 71 |
| 40 | 39.94 | 23.61 | 164 | 99 | 2002 | 5.47 | 75 |
| 40 | 32.35 | 21.53 | 163 | 97 | 2070 | 7.59 | 75 |

The above acquisition layers were tested on identical commercial diapers at ambient (20° C.) and body (37° C.) temperatures. The original topsheet and acquisition layers were removed and replaced by a 20 gsm thermal bonded 2.2 denier polypropylene fiber topsheet and one of the acquisition layers from the above table. A test was run on each article to determine the ability of the article to absorb three successive insults of 100 ml of synthetic urine. The results, for diapers having a liquid transfer layer basis weight of about 30 and 40 gsm, respectively, are shown in the following two tables.

| NOMINAL BASIS WEIGHT 30 gsm | | | | |
|---|---|---|---|---|
| Tg (C.) of Binder | 1st Insult (sec) | 2nd Insult (sec) | 3rd Insult (sec) | Fluid Temp. |
| 20 | 50 | 54 | 58 | Ambient (20 C.) |
| 30 | 47 | 55 | 58 | Ambient (20 C.) |
| 40 | 40 | 46 | 48 | Ambient (20 C.) |
| 20 | 39 | 45 | 54 | Body (37 C.) |
| 30 | 43 | 49 | 55 | Body (37 C.) |
| 40 | 36 | 36 | 38 | Body (37 C.) |

| NOMINAL BASIS WEIGHT 30 gsm | | | | |
|---|---|---|---|---|
| Tg (C.) | 1st Insult (sec) | 2nd Insult (sec) | 3rd Insult (sec) | Saline Temp. |
| 20 | 41 | 49 | 54 | Ambient (20 C.) |
| 40 | 36 | 41 | 45 | Ambient (20 C.) |
| 20 | 39 | 43 | 43 | Body (37 C.) |
| 40 | 27 | 32 | 38 | Body (37 C.) |

The time in seconds is the time required for each dose or insult of liquid to be absorbed into the article, and it will be noted that acquisition times are significantly lower when the article included a transfer layer having a binder Tg in excess of 30°, with best results shown at a Tg of 40° C.

What is claimed is:

1. An absorbent article comprising a liquid absorbing core, a porous cover sheet over said core, and a liquid acquisition layer disposed between said core and cover sheet, said liquid acquisition layer comprising a porous nonwoven fabric and an adhesive bonding said fabric together, said adhesive having a glass transition temperature of greater than 30° C.

2. In combination with a disposable absorbent product having a porous cover sheet and an absorbent core, a liquid acquisition layer comprising a nonwoven fabric having a basis weight of from about 15 to about 60 gsm, said fabric comprising polymer staple fibers, a cured adhesive resin bonding said fibers, said adhesive resin having a glass transition temperature, said temperature being in excess of 30° C., and said layer disposed between said porous cover sheet and said absorbent core.

3. The combination of claim 2 wherein said cover sheet of said disposable absorbent product is a bonded nonwoven web of polymer staple fibers, the fibers of said cover sheet having a smaller denier than the fibers in said liquid acquisition layer.

4. A disposable absorbent product having a porous cover sheet, an absorbent core and a liquid acquisition layer, said layer comprising a nonwoven fabric having a basis weight of from about 15 to about 60 gsm, said fabric comprising polymer staple fibers, a cured adhesive resin bonding said fibers, said adhesive resin having a glass transition temperature, said temperature being in excess of 30° C., said layer being disposed between said porous cover sheet and said absorbent core.

5. The disposable absorbent product claim 4 wherein said cover sheet is a bonded nonwoven web of polymer staple fibers, the fibers of said cover sheet having a smaller denier than the fibers in said liquid acquisition layer.

* * * * *